US012715892B2

(12) United States Patent
Kuusisto et al.

(10) Patent No.: US 12,715,892 B2
(45) Date of Patent: Aug. 25, 2026

(54) PROCESS FOR PURIFYING A HUMAN MILK OLIGOSACCHARIDE AND RELATED COMPOSITIONS

(71) Applicant: INBIOSE N.V., Zwijnaarde (BE)

(72) Inventors: Jyrki Kuusisto, Kantvik (FI); Jari Lewandowski, Kantvik (FI); Antti Koponen, Kantvik (FI); Tero Tuomas Mentunen, Kantvik (FI); Wim Soetaert, Zwijnaarde (BE)

(73) Assignee: INBIOSE N.V., Zwijnaarde (BE)

( * ) Notice: Subject to any disclaimer, the term of this patent is extended or adjusted under 35 U.S.C. 154(b) by 562 days.

(21) Appl. No.: 18/247,118

(22) PCT Filed: Sep. 28, 2021

(86) PCT No.: PCT/US2021/052353
§ 371 (c)(1),
(2) Date: Mar. 29, 2023

(87) PCT Pub. No.: WO2022/072323
PCT Pub. Date: Apr. 7, 2022

(65) Prior Publication Data

US 2023/0406875 A1 Dec. 21, 2023

Related U.S. Application Data

(60) Provisional application No. 63/084,818, filed on Sep. 29, 2020.

(30) Foreign Application Priority Data

Oct. 19, 2020 (EP) .................................... 20202534

(51) Int. Cl.
*C07H 1/08* (2006.01)
*A23L 33/00* (2016.01)
*A23L 33/125* (2016.01)
*C07H 3/06* (2006.01)

(52) U.S. Cl.
CPC .............. *C07H 1/08* (2013.01); *A23L 33/125* (2016.08); *A23L 33/40* (2016.08); *C07H 3/06* (2013.01)

(58) Field of Classification Search
CPC .... C07H 3/06; C07H 1/06; C07H 1/08; A23L 33/40; A23L 33/125; A23L 5/00; A23L 5/273
USPC ........ 426/801; 210/650, 651, 681, 645, 786, 210/290
See application file for complete search history.

(56) References Cited

U.S. PATENT DOCUMENTS 10,377,787 B2 * 8/2019 Jennewein ............... C07H 1/08
11,377,462 B2 * 7/2022 Dijkstra ................... C07H 1/08

FOREIGN PATENT DOCUMENTS

WO 2018/164937 A1 9/2018
WO WO-2019063757 A1 * 4/2019 ............... C07H 1/08
WO 2020/154565 A1 7/2020

OTHER PUBLICATIONS

International Search Report for International Application No. PCT/US2021/052353, mailed Dec. 14, 2021, 4 pages.
International Written Opinion for International Application No. PCT/US2021/052353, mailed Dec. 14, 2021, 9 pages.

* cited by examiner

*Primary Examiner* — Hong T Yoo
(74) *Attorney, Agent, or Firm* — TraskBritt

(57) ABSTRACT

This specification relates to a process for preparing a purified human milk oligosaccharide ("HMO") from an HMO-containing solution (e.g., a fermentation broth) by a process comprising mixed bed ion exchange, and a product of such a process.

26 Claims, No Drawings

PROCESS FOR PURIFYING A HUMAN MILK OLIGOSACCHARIDE AND RELATED COMPOSITIONS

CROSS-REFERENCE TO RELATED APPLICATIONS

This application is a national phase entry under 35 U.S.C. § 371 of International Patent Application PCT/US2021/052353, filed Sep. 28, 2021, designating the United States of America and published as International Patent Publication WO 2022/072323 A1 on Apr. 7, 2022, which claims the benefit under Article 8 of the Patent Cooperation Treaty to U.S. Patent Application Ser. No. 63/084,818, filed Sep. 29, 2020 and European Patent Application Serial No. 20202534.2, filed Oct. 19, 2020. The entire text of each of the above-referenced patent applications is incorporated by reference into this specification.

TECHNICAL FIELD

This specification relates to purifying a human milk oligosaccharide ("HMO") from an HMO-containing solution (e.g., a fermentation broth) by a process comprising mixed bed ion exchange, and a product of such a process.

BACKGROUND

Human milk oligosaccharides are important for nutrition and therapeutics. HMOs include, for example, 2'-fucosyllactose ("2'-FL"), 3-fucosyllactose ("3-FL"), lacto-N-tetraose ("LNT"), 6'-sialyllactose ("6'-SL"), 3'-sialyllactose ("3'-SL"), difucosyllactose ("DiFL" or "LDFT"), lacto-N-neotetraose ("LNnT"), lacto-N-fucopentaose, lacto-N-difucohexaose, lacto-N-neodifucohexaose, lacto-N-neooctaose, lacto-N-fucopentaose, lacto-N-neofucopentaose, 3' sialyl-3-fucosyllactose, sialyl-lacto-N-tetraose, LS-tetrasaccharide, lacto-N-triose, lacto-N-neofucopentaose, lacto-N-neofucopentaose, lacto-N-difucohexaose, 6'-galactosyllactose, 3'-galactosyllactose, lacto-N-hexaose and lacto-N-neohexaose. Many HMOs in human breast milk are fucosylated, unlike oligosaccharides produced by, for example, dairy animals. The most abundant HMO in human breast milk is 2'-FL.

HMO are composed of the five monosaccharide building blocks D-glucose (Glc), D-galactose (Gal), N-acetylglucosamine (GlcNAc), L-fucose (Fuc) and sialic acid (N-acetylneuraminic acid). They can be grouped into neutral and charged oligosaccharides, the latter being sialylated. Neutral fucosylated HMOs are neutral and contain fucose at the terminal position (e.g., 2'-fucosyllactose (2'-FL) and lactodifucopentaose). They represent 35% to 50% of the total HMO content. Neutral N-containing (nonfucosylated) HMOs are neutral and contain N-acetylglucosamine at the terminal position (e.g., lacto-N-tetraose), and represent 42% to 55% of the total HMO content. Neutral HMOs account for more than 75% of the total HMOs in human breast milk.

Acid (sialylated) HMOs are acidic and contain sialic acid at the terminal position (e.g., 2'-sialyllactose). They represent 12% to 14% of the total HMO content.

Many recent approaches for synthesizing HMOs involve microbial fermentation processes, which produce HMOs (such as 2'-FL, 3-FL, LNT, 3'-SL and 6'-SL) from lactose. In such a process, a given HMO is synthesized by cultured microorganisms, such as recombinant *E. coli*. The HMO is then isolated from the broth of biomolecules produced by the culture through a series of purification processes. While there has been success with this approach, the fermentation processes generally produce a complex product mixture which includes, besides the desired HMO(s), other ingredients, such as monovalent and divalent salts, lactose, oligosaccharides, monosaccharides, amino acids, polypeptides, proteins, organic acids, nucleic acids, processing aids, etc.

HMOs may be incorporated into a food (e.g., human or pet food), dietary supplement or medicine. HMOs are particularly useful in, for example, infant formula. Thus, there is need for HMOs that are substantially pure.

Accordingly, a need continues to exist for effective, reliable and economically and environmentally feasible processes in industrial scale to provide an HMO product of high quality and purity and good yield.

BRIEF SUMMARY

Briefly, this specification generally provides, in part, a process for making a purified human milk oligosaccharide ("HMO") from an HMO solution derived from a fermentation process. The process comprises passing the HMO solution through a mixed bed ion exchange vessel comprising a combination of cation ion exchange material with anion ion exchange material. The process is carried out in the absence of any ion exchange vessel that comprises cation ion exchange material without also comprising anion ion exchange material. And the process is carried out in the absence of any ion exchange vessel that comprises anion ion exchange material without also comprising cation ion exchange material.

This specification also provides, in part, a purified HMO (or mixture of HMOs) obtained by the above-referenced process.

This specification also provides, in part, a process for making a food, dietary supplement, infant formula or medicine. The process comprises preparing a purified HMO according to the above-described process, and mixing the purified HMO with an ingredient suitable for the food, dietary supplement, infant formula or medicine.

This specification also provides, in part, a food, dietary supplement, infant formula or medicine prepared by such a process.

Further benefits of the teachings of this specification will be apparent to one skilled in the art from reading this specification.

DETAILED DESCRIPTION

This detailed description is intended to acquaint others skilled in the art with the disclosure, its principles, and its practical application so that others skilled in the art may adapt and apply the disclosure in its numerous forms, as they may be best suited to the requirements of a particular use. This detailed description and its specific examples, while indicating certain embodiments, are intended for purposes of illustration only. This specification, therefore, is not limited to the described embodiments, and may be variously modified.

Definitions

The term "2'-FL" or "2'FL" refers to 2'-fucosyllactose (also referred to as "2'-O-fucosyllactose").

The term "3-FL" or "3FL" refers to 3-fucosyllactose (also referred to as "3-O-fucosyllactose").

The term "HMO" refers to human milk oligosaccharide.

The term "neutral HMO" refers to fucosylated (contain fucose at the terminal position) and non-fucosylated (N-containing, contain N-acetylglucosamine at the terminal position) HMOs.

The term "ICUMSA" refers to "International Commission for Uniform Process of Sugar Analysis" sugar color grading system.

The term "MB" refers to a mixed bed.

The term "IEX" refer to ion exchange.

The term "SAC" refers to strong acid cation ion exchange material (e.g., resin).

The term "WBA" refers to weak base anion ion exchange material (e.g., resin).

The term "SBA" refers to strong base anion ion exchange material (e.g., resin).

The term "WAC" refers to weak acid cation ion exchange material (e.g., resin).

A "mixed bed ion exchange vessel" or "MB ion exchange vessel" is an ion exchange vessel (e.g., a column) that comprises a combination of cation ion exchange material (e.g., resin) with anion ion exchange material (e.g., resin).

Human Milk Oligosaccharide

There are over 150 known human milk oligosaccharides generally present in human breast milk. A process described in this specification may be used to prepare a single purified HMO or a purified mixture of two or more HMOs.

In some embodiments, a process of this specification comprises preparing a purified HMO selected from fucosyllactoses (such 2'-FL, 3-FL or DiFL), LNT, LNnT, lacto-N-fucopentaose, lacto-N-difucohexaose, lacto-N-neodifucohexaose, lacto-N-neooctaose, lacto-N-fucopentaose, lacto-N-neofucopentaose, LS-tetrasaccharide, lacto-N-triose, lacto-N-neo fucopentaose, lacto-N-neofucopentaose, lacto-N-difucohexaose, 6'-galactosyllactose, 3'-galactosyllactose, lacto-N-hexaose or lacto-N-neohexaose. In some embodiments, a process of this specification comprises preparing a purified HMO mixture comprising one or more of the above-listed HMOs. In some embodiments, a process of this specification comprises preparing a purified HMO mixture comprising at least two of the above-listed HMOs.

In some embodiments, a process of this specification is used to prepare a purified neutral HMO.

In some embodiments, a process of this specification is used to prepare a purified HMO selected from a fucosyllactose (e.g., 2'-FL, 3-FL or DiFL) or N-containing (nonfucosylated) HMO (e.g., LNT or LNnT).

In some embodiments, a process of this specification is used to prepare a purified fucosyllactose (also referred to as "FL"). At room temperature and pressure, a fucosyllactose is typically a white to ivory colored solid and soluble in water. In some embodiments, the purified fucosyllactose is 2'-FL. In some embodiments, the purified fucosyllactose is 3-FL. In some embodiments, a process of this specification is used to prepare a purified HMO mixture comprising a fucosyllactose. In some embodiments, a process of this specification is used to prepare a purified HMO mixture comprising 2'-FL, 3-FL or DiFL. In some embodiments, a process of this specification is used to prepare a purified HMO mixture comprising at least two fucosyllactoses. In some embodiments, a process of this specification is used to prepare a purified HMO mixture comprising 2'-FL and DiFL.

In some embodiments, a process of this specification comprises preparing purified LNT. In some embodiments, the process of this specification is used to make a purified HMO mixture comprising LNT.

In some embodiments, a process of this specification comprises preparing purified LNnT. In some embodiments, the process of this specification is used to make a purified HMO mixture comprising LNnT.

HMO Solution

An "HMO solution" from which an HMO is purified in accordance with this specification generally comprises an aqueous medium. The aqueous medium comprises both the HMO and other ingredients, for example, monovalent and divalent salts, lactose, oligosaccharides (other than HMO), monosaccharides, amino acids, polypeptides, proteins, organic acids and nucleic acids.

In some embodiments, the aqueous medium is water.

In some embodiments, the HMO is selected from 2'-FL, 3-FL, LNT, DiFL, LNnT, lacto-N-fucopentaose, lacto-N-difucohexaose, lacto-N-neodifucohexaose, lacto-N-neooctaose, lacto-N-fucopentaose, lacto-N-neofucopentaose, LS-tetrasaccharide, lacto-N-triose, lacto-N-neo fucopentaose, lacto-N-neofucopentaose, lacto-N-difucohexaose, 6'-galactosyllactose, 3'-galactosyllactose, lacto-N-hexaose, and lacto-N-neohexaose.

In some embodiments, the HMO is a fucosyllactose.

In some embodiments, the HMO is 2'-FL.

In some embodiments, the HMO is 3-FL.

In some embodiments, the HMO is DiFL.

In some embodiments, the HMO is LNnT.

In some embodiments, the HMO is LNT.

In some embodiments, the HMO solution comprises at least two HMOs. In some embodiments, the HMO solution comprises at least three HMOs. In some embodiments, the HMO solution comprises at least four HMOs. In some embodiments, the HMO solution comprises at least five HMOs.

In some embodiments, the HMO solution comprises two or more HMOs selected from fucosyllactoses, LNnT and LNT. In some such embodiments, the fucosyllactoses are selected from 2'-FL, DiFL and 3-FL.

In some embodiments, the HMO solution comprises 2'-FL and 3-FL.

In some embodiments, the HMO solution comprises 2'-FL and DiFL.

Typically, the HMO solution further comprises one or more ingredients in addition to the HMO(s) to be purified. Such other ingredients may include, for example, monovalent and divalent salts, lactose, oligosaccharides, monosaccharides, amino acids, polypeptides, proteins, organic acids, nucleic acids, etc.

In some embodiments, the HMO solution comprises (in addition to the HMO(s) to be purified) one or more additional HMOs and/or one or more other types of carbohydrates.

In some embodiments, the HMO solution comprises (in addition to the HMO(s) to be purified) one or more oligosaccharides.

In some embodiments, the HMO solution comprises (in addition to the HMO(s) to be purified) one or more additional HMOs.

In some embodiments, the HMO solution comprises (in addition to the HMO(s) to be purified) one or more additional HMOs selected from 2'-FL, 3-FL, LNT, DiFL, LNnT, lacto-N-fucopentaose, lacto-N-difucohexaose, lacto-N-neodifucohexaose, lacto-N-neooctaose, lacto-N-fucopentaose, lacto-N-neofucopentaose, LS-tetrasaccharide, lacto-N-triose, lacto-N-neo fucopentaose, lacto-N-neofucopentaose, lacto-N-difucohexaose, 6'-galactosyllactose, 3'-galactosyllactose, lacto-N-hexaose, and lacto-N-neohexaose.

In some embodiments, the HMO solution comprises (in addition to the HMO(s) to be purified) 2'-O-fucosyl lactulose.

In some embodiments, the HMO solution comprises (in addition to the HMO(s) to be purified) DiFL.

In some embodiments, the HMO solution comprises (in addition to the HMO(s) to be purified) lactose.

In some embodiments, the HMO solution comprises (in addition to the HMO(s) to be purified) lactulose.

In some embodiments, the HMO solution comprises (in addition to the HMO(s) to be purified) one or more monosaccharides.

In some embodiments, the HMO solution comprises (in addition to the HMO(s) to be purified) fucose.

In some embodiments, the HMO solution comprises (in addition to the HMO(s) to be purified and the second carbohydrate) glucose.

In some embodiments, the HMO solution comprises (in addition to the HMO(s) to be purified) galactose.

In some embodiments, the HMO solution comprises (in addition to the HMO(s) to be purified) one or more monovalent salts.

In some embodiments, the HMO solution comprises (in addition to the HMO(s) to be purified) one or more divalent salts.

In some embodiments, the HMO solution comprises (in addition to the HMO(s) to be purified) one or more amino acids.

In some embodiments, the HMO solution comprises (in addition to the HMO(s) to be purified) one or more proteins.

In some embodiments, the HMO solution comprises (in addition to the HMO(s) to be purified) one or more organic acids.

In some embodiments, the HMO solution comprises (in addition to the HMO(s) to be purified) one or more nucleic acids.

In some embodiments, the HMO solution comprises (or is derived in whole or in part from) a product of a fermentation. In some such embodiments, the HMO solution is (or derived in whole or in part from) the product of a fermentation used to make the HMO(s) to be purified. In some such embodiments, the other carbohydrate(s) in the solution is/are from the culture medium used in the fermentation and/or formed during and/or after the fermentation. In some embodiments, the fermentation comprises culturing, in an aqueous culture medium comprising a carbohydrate (such as lactose and/or fucose), a recombinant microorganism comprising at least one recombinant polynucleotide sequence encoding an enzyme capable of producing an HMO. The product of the fermentation process may be referred to as a fermentation "product" or "broth."

The fermentation product typically comprises many ingredients in addition to the HMO(s) to be purified. Such ingredients may include, for example, monovalent and divalent salts, lactose, oligosaccharides, monosaccharides, amino acids, polypeptides, proteins, organic acids, nucleic acids, etc.

In some embodiments, the fermentation product comprises one or more ingredients selected from divalent salts, lactose, oligosaccharides besides the HMO(s) to be purified, monosaccharides, amino acids, polypeptides, proteins, organic acids and nucleic acids. In some embodiments, the fermentation product comprises a divalent salt, lactose, an oligosaccharide besides the HMO(s) to be purified, a monosaccharide, an amino acid, a polypeptide, a protein, an organic acid and a nucleic acid.

In some embodiments, the fermentation product comprises one or more ingredients selected from salts, acids, human milk oligosaccharides besides the HMO(s) to be purified, lactose and monomeric sugars. In some embodiments, the fermentation product comprises a salt, an acid, a human milk oligosaccharide besides the HMO(s) to be purified, lactose and a monomeric sugar.

In some embodiments, an HMO to be purified is a fucosyllactose, and the HMO solution comprises (or is derived in whole or in part from) a product of a fermentation process wherein the fermentation process comprises culturing, in an aqueous culture medium comprising a carbohydrate (such as lactose and/or fucose), a recombinant microorganism comprising a recombinant polynucleotide sequence encoding an α-1,2-fucosyl transferase (EC 2.4.1.69) or α-1,3-fucosyl transferase (EC 2.4.1.214).

In general, when the HMO solution comprises (or is derived in whole or in part from) a product of a fermentation process, the process of this specification generally comprises one or more process steps wherein the cell biomass of the microorganisms used in the fermentation is separated from the fermentation product. In general, at least a portion (or all) of the cell mass is removed before the ion exchange.

Cell biomass may be separated from a fermentation product using, for example, filtration, centrifugation, sedimentation and/or other process suitable for removing cell biomass.

In some embodiments, separation of microorganisms from a fermentation product comprises ultrafiltration (also referred to as "UF"). Ultrafiltration can also be particularly beneficial to, for example, remove large biomolecules, such as endotoxins, proteins, nucleic acids and lipopolysaccharides.

In some embodiments, the ultrafiltration is carried out using a cross-flow filtration. The polymeric membrane configuration used can be, for example, a spiral wound, hollow fiber or plate and frame unit. The ultrafiltration can also be carried out with tubular or ceramic disc membranes. Typically, the ultrafiltration membrane pore size can be chosen from about 0.1 to about 0.001 μm, or from about 200 kD to about 1 kD.

In some embodiments, separation of microorganisms from a fermentation product comprises cross-flow microfiltration (also referred to as "MF"). Typically, the MF membrane pore size is from about 0.1 μm to about 3 μm. The polymeric membrane configuration used can be, for example, a spiral wound, hollow fiber or plate and frame unit. The cross-flow microfiltration can also be carried out with ceramic tubular or ceramic disc membranes. Furthermore, MF membranes made of steel can be used.

In some embodiments, separation of microorganisms from a fermentation product comprises centrifugation. Typically, such a centrifugation may be carried out using disc stack separator reaching from about 3000 to about 20000 G-force. The clarified solution can be further purified with, for example, filtration technologies to obtain liquid essentially free of microbes.

In some embodiments, the cell biomass removal is carried out at a temperature from about 5° C. to about 20° C.

In some embodiments, the cell biomass removal is carried out at a temperature of no greater than about 18° C. In some embodiments, the cell biomass removal is carried out at a temperature of no greater than about 16° C. In some embodiments, the cell biomass removal is carried out at a temperature of less than about 16° C. In some embodiments, the cell biomass removal is carried out at a temperature of no greater than about 15° C. In some embodiments, the cell biomass removal is carried out at a temperature of less than about 15° C. In some embodiments, the cell biomass removal is carried out at a temperature of no greater than about 10° C. In some embodiments, the cell biomass removal is carried out at a temperature of less than about 10° C. In some embodiments, the cell biomass removal is carried out at a temperature of no greater than about 9° C. In some embodiments, the cell biomass removal is carried out at a temperature of less than about 9° C. In some embodiments, the cell biomass removal is carried out at a temperature of no greater than about 8° C. In some embodiments, the cell biomass removal is carried out at a temperature of less than about 8° C. In some embodiments, the cell biomass removal is carried out at a temperature of no greater than about 7° C. In some embodiments, the cell biomass removal is carried out at a temperature of less than about 7° C. In some embodiments, the cell biomass removal is carried out at a temperature of no greater than about 6° C. In some embodiments, the cell biomass removal is carried out at a temperature of less than about 6° C. In some embodiments, the cell biomass removal is carried out at a temperature of no greater than about 5° C. In some embodiments, the cell biomass removal is carried out at a temperature of less than about 5° C.

Ion Exchange

The process of this specification generally comprises passing the HMO solution through a mixed bed ion exchange comprising a combination of cation ion exchange material (e.g., resin) with anion ion exchange material (e.g., resin). The process is carried out in the absence of any ion exchange step that comprises use of cation ion exchange material in the absence of an anion ion exchange material. And the process is carried out in the absence of any ion exchange step that comprises use of anion ion exchange material in the absence of a cation ion exchange material.

Ion exchange is generally a reversible interchange of ions between a solid ion exchange material (or "ion exchanger") and a liquid such as water. The ion exchange reaction typically occurs in an ion exchange vessel (often an ion exchange column), where a process solution is passed through the solid that facilitates the exchange of ions. There is generally no permanent change in the structure of the solid. Ion exchange is used in water treatment and also provides a method of separation in many non-water processes. It is widely used in chemical synthesis, medical research, food processing, mining, agriculture and a variety of other areas.

The ion exchange material is generally an insoluble solid material (often a specialized resin) which carries exchangeable cations or anions. The ions can be exchanged for a stoichiometrically equivalent number of other ions of the same electrical charge when the ion exchange material is in contact with an electrolyte solution. Carriers of exchangeable cations are called cation ion exchangers, and carriers of exchangeable anions are called anion ion exchangers. Ion exchange resins are polymers that are capable of exchanging ions with ions in a solution that is passed through them. Mixed bed ion exchange resin comprises a mixture of cation ion exchange resin and anion ion exchange resin.

Strong acid cation (SAC) exchange resins may be, for example, polystyrene based resins with sulfonic acid as functional group.

Weak acid cation (WAC) exchange resins may be, for example, polyacrylic based resins with formic acid as functional group.

Strong base anion (SBA) exchange resins may be, for example, polystyrene or polyacrylic based resins. SBA resins are often categorized as Type 1 and Type 2, based on the functional group used. Type 1 resins generally have trimethylamine as functional group. Type 2 resins generally have dimethyl ethanolamine as a functional group.

Weak base anion (WBA) exchange resins may be, for example, polystyrene or polyacrylic based resins with tertiary amine as a functional group.

In some embodiments, the mixed bed ion exchange is conducted after removal of cell biomass.

In some embodiments, the mixed bed ion exchange is conducted after an ultrafiltration step.

In some embodiments, the mixed bed ion exchange is conducted after a nanofiltration step.

In some embodiments, the mixed bed ion exchange is conducted before a nanofiltration step.

In some embodiments, the mixed bed ion exchange is conducted after an active carbon treatment step.

In some embodiments, the mixed bed ion exchange is conducted before an active carbon treatment step.

In some embodiments, the mixed bed ion exchange is conducted after an evaporation step.

In some embodiments, the mixed bed ion exchange is conducted before an evaporation step.

In some embodiments, the mixed ion exchange is conducted after an electrodialysis step.

In some embodiments, the mixed bed ion exchange is conducted before an electrodialysis step.

In some embodiments, the mixed bed ion exchange is conducted after an antifoam removal step.

In some embodiments, the mixed bed ion exchange is conducted before an antifoam removal step.

In some embodiments, the ion exchange is conducted after dissolving the HMO. In some such embodiments, for example, the HMO to be purified comprises a previously crystalline or spray dried HMO. Here, the HMO may be first dissolved, and then the resulting solution is passed through the mixed bed resin.

In some embodiments, ion exchange is conducted for reprocessing dissolved crystalline product.

In some embodiments, ion-exchange is conducted for reprocessing dissolved spray dried product.

In some embodiments, the feed solution for the mixed bed ion exchange is, for example, a fermentation broth after cell removal, permeate from ultrafiltration, concentrate from nanofiltration, or product of an active carbon treatment.

A final HMO product of the process disclosed herein may be, for example, a syrup, spray dried powder or crystalline product.

In some embodiments, the mixed bed ion exchange disclosed herein is used to make a final HMO product.

In general, mixed bed ion exchange is the only ion exchange used in the ion exchange step(s) of the HMO solution purification of this specification.

In some embodiments, one mixed bed ion exchange vessel (e.g., column) is used.

In some embodiments, at least two mixed bed ion exchange vessels (e.g., columns) are used. In such embodiments, the multiple vessels may be used in parallel and/or in series. And, to the extent used in series, the vessels may be directly connected to each other and/or separated from each other by one or more other purification steps (e.g., nanofiltration, electrodialysis, chromatography, antifoam removal, activated carbon, sterile filtration, crystallization, spray-drying, evaporation, etc.).

In some embodiments, two mixed bed ion exchange vessels are used in parallel. In some embodiments, two mixed bed ion exchange vessels are used in series. In some embodiments, three or more mixed bed ion exchange vessels are used. In some embodiments, three or more mixed bed ion exchange vessels are used in series.

In some embodiments, the cation ion exchange resin and anion ion exchange resin are mixed before packing into a mixed bed ion exchange column. The mixed bed resin may be mixed before packing to the column from a selected cation ion exchange resin and a selected anion ion exchange resin in a selected volume ratio. In some embodiments, the mixture that is packed into the mixed bed ion exchange column is a uniform mixture. Mixed bed resins are also available as a ready-mixed resin, for example, AMBERTEC™ UP6040 by DuPont.

In some embodiments, the cation ion exchange resin and anion ion exchange resin are packed in the column in alternating layers. In some embodiments, each layer has the same volume. In other embodiments, the layers have different volumes. In some embodiments, the cation ion exchange resin and anion ion exchange resin are packed in the column in 6 or more alternating layers. In some embodiments, the cation ion exchange resin and anion ion exchange resin are packed in the column in 30 or more alternating layers. In some embodiments, the cation ion exchange resin and anion ion exchange resin are packed in the column in 100 or more alternating layers.

The mixed ion exchange bed vessel (e.g., column) is generally packed with cation ion exchange material (e.g., cation ion exchange resin) and anion ion exchange material (e.g., anion ion exchange resin). In some embodiments, the volume ratio of cation ion exchange material to anion ion exchange resin is from about 10:90 to about 90:10. In some embodiments, the ratio is from about 30:70 to about 70:30. In some embodiments, the ratio is from about 20:80 to about 80:20. In some embodiments, the ratio is from about 40:60 to about 60:40. In some embodiments, the ratio is about 50:50. In some embodiments, the ratio is selected based on the properties of the feed liquor fed to the ion exchange system.

In some embodiments, the mixed bed column is packed with strong acid cation (SAC) and strong base anion (SBA) ion exchange resins. In some embodiments, SAC:SBA resin volume ratio is from about 10:90 to about 90:10. In some embodiments, SAC:SBA resin volume ratio is from about 30:70 to about 70:30. In some embodiments, SAC:SBA resin volume ratio is from about 20:80 to about 80:20. In some embodiments, SAC:SBA resin volume ratio is from about 40:60 to about 60:40. In some embodiments, SAC:SBA resin volume ratio is about 50:50. In some embodiments, resin volume ratio is selected based on the properties of the feed liquor fed to the ion exchange system.

In some embodiments, mixed column is packed with strong acid cation (SAC) and weak base anion (WBA) ion exchange resins. In some embodiments, SAC:WBA resin volume ratio is from about 10:90 to about 90:10. In some embodiments, SAC:WBA resin volume ratio is from about 30:70 to about 70:30. In some embodiments, SAC:WBA resin volume ratio is from about 20:80 to about 80:20. In some embodiments, SAC:WBA resin volume ratio is from about 40:60 to about 60:40. In some embodiments, SAC:WBA resin volume ratio is about 50:50. In some embodiments, resin volume ratio is selected based on the properties of the feed liquor fed to the ion exchange system.

In some embodiments, the mixed bed column is packed with strong acid cation (WAC) and strong base anion (WBA) ion exchange resins. In some embodiments, WAC:WBA resin volume ratio is from about 10:90 to about 90:10. In some embodiments, WAC:WBA resin volume ratio is from about 30:70 to about 70:30. In some embodiments, WAC:WBA resin volume ratio is from about 20:80 to about 80:20. In some embodiments, WAC:WBA resin volume ratio is from about 40:60 to about 60:40. In some embodiments, WAC:WBA resin volume ratio is about 50:50. In some embodiments, resin volume ratio is selected based on the properties of the feed liquor fed to the ion exchange system.

In some embodiments, the mixed bed column is packed with strong acid cation (WAC) and strong base anion (SBA) ion exchange resins. In some embodiments, WAC:SBA resin volume ratio is from about 10:90 to about 90:10. In some embodiments, WAC:SBA resin volume ratio is from about 30:70 to about 70:30. In some embodiments, WAC:SBA resin volume ratio is from about 20:80 to about 80:20. In some embodiments, WAC:SBA resin volume ratio is from about 40:60 to about 60:40. In some embodiments, WAC:SBA resin volume ratio is about 50:50. In some embodiments, resin volume ratio is selected based on the properties of the feed liquor fed to the ion exchange system.

In some embodiments, the SAC resin is in the $H^+$-ion form.

In some embodiments, the SAC resin is in the $Na^+$-ion form.

In some embodiments, the WAC resin is in the $H^+$-ion form.

In some embodiments, the WAC resin is in the $Na^+$-ion form.

In some embodiments, the WBA resin is in the $OH^-$-ion form (also referred to as free base form).

In some embodiments, the WBA resin is in the $Cl^-$-ion form.

In some embodiments, the SBA resin is in the $OH^-$-ion form (also referred to as free base form).

In some embodiments, the SBA resin is in the $Cl^-$-ion form.

HMOs have varying stabilities. In general, HMO stability is dependent on pH. Typically, stability of an HMO solution is better in a slightly acidic (at a pH of from about 4.5 to about 6) or neutral (at about pH 7) pH range.

In some embodiments, a mixed bed ion exchange is used for adjusting pH of the HMO solution. In some embodiments, pH adjustment of the process stream with acid or alkali addition is avoided by using the mixed bed ion exchanger to adjust the pH. In some embodiments, mixed bed ion exchange is used to neutralize the HMO solution.

In some embodiments, the pH of the HMO stream at the exit of the mixed bed ion exchange vessel is from about 4.5 to about 7. In some embodiments, the pH of the HMO stream at the exit of the mixed bed ion exchange vessel is from about 4.5 to about 6. In some embodiments, the pH of the HMO stream at the exit of the mixed bed ion exchange vessel is from about 6 to about 7.

HMO stability is also generally dependent on temperature. In some embodiments, the temperature during the ion exchange step(s) is from about 0° C. to about 60° C. In some embodiments, the temperature during the ion exchange step(s) is from about 5° C. to about room temperature. In some embodiments, the temperature during the ion exchange step(s) is from about 5° C. to about 25° C. In some embodiments, the temperature during the ion exchange step(s) is from about 5° C. to about 20° C. In some embodiments, the temperature during the ion exchange step(s) is from about 0° C. to about 10° C. In some embodiments, the temperature during the ion exchange step(s) is from about 5° C. to about 10° C. In some embodiments, the temperature during the ion exchange step(s) is about 10° C. In some embodiments, the temperature during the ion exchange step(s) is about 5° C.

In some embodiments, the dry substance concentration in the HMO solution is from about 3 to about 65 g/100 g when the solution is fed into an ion exchange step described herein. In some embodiments, the dry substance concentration in the HMO solution is from about 3 to about 60 g/100 g when the solution is fed into an ion exchange step described herein. In some embodiments, the dry substance concentration in the HMO solution is from about 3 to about 50 g/100 g when the solution is fed into an ion exchange step described herein. In some embodiments, the dry substance concentration in the HMO solution is from about 12 to about 20 g/100 g when the solution is fed into an ion exchange step described herein. In some embodiments, the dry substance concentration in the HMO solution is from about 3 to about 30 g/100 g when the solution is fed into an ion exchange step described herein. In some embodiments, the dry substance concentration in the HMO solution is from about 5 to about 50 g/100 g when the solution is fed into an ion exchange step described herein.

In some embodiments, the flowrate through the mixed bed ion exchange column is from about 0.5 BV/h to about 10 BV/h or greater. In some embodiments, the flowrate through the mixed bed ion exchange column is from about 2 BV/h to about 5 BV/h. In some embodiments, the flowrate through the mixed bed ion exchange column is from about 2 BV/h to about 3 BV/h. In some embodiments, the flowrate through the mixed bed ion exchange column is about 2 BV/h. In some embodiments, the flowrate through the mixed bed ion exchange column is about 2.5 BV/h. In some embodiments, the flowrate through the mixed bed ion exchange column is about 3 BV/h.

In some embodiments, the HMO yield using a process of this specification is greater than 80%. In some embodiments, the HMO yield is greater than 85%. In some embodiments, the HMO yield is greater than 90%. In some embodiments, the HMO yield is greater than 95%. In some embodiments, the HMO yield is greater than 97%.

Cationic compounds, anionic compounds and color and conductivity can generally be efficiently removed (or at least diminished) by using a mixed bed column. In some embodiments, the mixed bed ion exchange column is used to reprocess an HMO product that falls outside the desired product specification. In some embodiments, a mixed bed column is used to reprocess an HMO product that has too high pH. In some embodiments, a mixed bed column is used to reprocess an HMO product that has too low pH. In some embodiments, a mixed bed column is used to reprocess an HMO product that has too much color. In some embodiments, a mixed bed column is used to reprocess an HMO product that contains microbial contaminants. In some embodiments, a mixed bed column is used to reprocess an HMO product that has too high conductivity. In some embodiments, a mixed bed column is used to reprocess an HMO product that has too high salt concentration.

Additional Treatments

In some embodiments, the HMO purification process comprises subjecting the HMO solution to one or more of the following treatments: an enzymatic treatment (e.g., enzymatic hydrolysis of lactose), ultrafiltration, nanofiltration, electrodialysis, chromatography, antifoam removal, activated carbon, sterile filtration, crystallization, evaporation and/or spray-drying.

The additional treatments may typically be carried out in various orders, as well as being repeated at different points in the process. In some embodiments, the process comprises a combination of at least three of the above additional treatments. In some embodiments, the process comprises a combination of at least four of the above additional treatments.

In some embodiments, the HMO solution is subjected to nanofiltration. In some embodiments, the nanofiltration is carried out under conditions discussed in WO2020/154565 (incorporated by reference into this specification).

In some embodiments, the HMO solution is subjected to an antifoam removal step. In some embodiments, the antifoam removal is carried out under conditions discussed in PCT/US20/48379 (incorporated by reference into this specification).

In some embodiments, the HMO solution is subjected to evaporation. This can be helpful, for example, to concentrate the HMO by removing a solvent (e.g., water). In some embodiments, evaporation is the final purification step of the desired HMO.

In some embodiments, the HMO solution is subjected to spray drying. In some embodiments, the spray-drying is carried out under conditions discussed in WO2019/160922 (incorporated by reference into this specification). In some embodiments, spray-drying is the final purification step for the desired HMO.

In some embodiments, the process comprises crystallization. In some embodiments, no organic solvent is used during the crystallization. In some embodiments, the crystallization comprises a crystallization process disclosed in WO2018/164937 (incorporated by reference into this specification). In some embodiments, crystallization is the final purification step of the desired HMO. In some embodiments, the process comprises both crystallization and evaporation. In some embodiments, the process comprises both crystallization and spray-drying.

In some embodiments, no base or acid is added to the HMO solution downstream of the mixed bed ion exchange before the HMO solution is passed through an enzymatic treatment, ultrafiltration, nanofiltration, sterile filtration, electrodialysis, chromatography, an antifoam removal step, activated carbon, crystallization or spray-drying. In some embodiments, no base or acid is added to the human milk oligosaccharide downstream of the mixed bed ion exchange.

EXAMPLES

The following examples are merely illustrative, and not limiting to the remainder of this specification in any way.

Color of the HMO solutions was measured at room temperature.

Example 1: 2'FL Purification Using MB Column Compared to Granular Carbon Column A fermentation-based solution containing various salts, acids, color, human milk oligosaccharides, lactose and monomeric sugars, which was first treated with SAC and WBA resins in separate columns connected in series, was treated with two different purification systems. The first purification system included a single mixed bed ion exchange column with SAC and SBA resins. The second purification system included a single column with activated carbon granule. The SAC resin was Dowex88, and the SBA resin was Dowex22. CHEMVIRON CPG was used as activated carbon.

Before the ion exchange process, the Dowex88 resin was regenerated with 5% sulfuric acid solution to the $H^+$ form, and the Dowex22 resin was regenerated with 4% NaOH solution to the $OH^-$ form. After each resin regeneration step, both resins were flushed with water to remove excess regeneration chemicals before the ion exchange process. In the first purification system, 250 mL of Dowex88 resin and 250 mL of Dowex22 resin were packed into a single MB column in alternating layers of the same volume. In the second purification system, 500 mL of CHEMVIRON CPG activated carbon was packed into a single column. A temperature of less than 25° C. was used in both systems.

The properties of the purification feed solution are shown in Table 1-1. The same feed solution was used in both purification systems. The properties of the outlet solution from the 250 mL SAC+250 mL SBA mixed bed ion exchange system are shown in Table 1-2 and the properties of the outlet solution from activated carbon purification system are shown in Table 1-3.

TABLE 1-1

| Properties of the purification feed solution | |
|---|---|
| Dry substance, g/100 g | 12.8 |
| pH | 9.4 |
| Conductivity, μS/cm | 35.4 |
| Color, ICUMSA | 188 |

TABLE 1-2

Properties of SAC + SBA mixed bed ion exchange system outlet

| Outlet fraction, BV | Dry substance, g/100 g | pH | Conductivity, μS/cm | Color, ICUMSA |
|---|---|---|---|---|
| 0-3 | 10.28 | 7.08 | 1.33 | 5 |
| 3-6 | 12.72 | 6.90 | 1.20 | 6 |
| 6-9 | 12.79 | 6.86 | 1.22 | 4 |
| 9-12 | 12.79 | 6.21 | 1.23 | 4 |
| 12-15 | 12.79 | 6.35 | 1.16 | 4 |
| 15-18 | 12.79 | 6.36 | 0.86 | 4 |

TABLE 1-3

Properties of activated carbon granule purification system outlet

| Outlet fraction, BV | Dry substance, g/100 g | pH | Conductivity, μS/cm | Color, ICUMSA |
|---|---|---|---|---|
| 0-3 | 9.11 | 6.78 | 46.5 | 8 |
| 3-6 | 11.89 | 6.49 | 56.5 | 4 |
| 6-9 | 12.53 | 6.87 | 56.6 | 4 |
| 9-12 | 12.66 | 6.92 | 56.6 | 6 |
| 12-15 | 12.72 | 7.04 | 56.6 | 6 |
| 15-18 | 12.79 | 6.86 | 56.8 | 6 |

Both purification methods were shown to adjust pH in between 6 and 7, and to remove 96-98% of the color. In addition, the mixed bed ion exchange system was also shown to remove conductivity. Conductivity removal was not shown with the activated carbon system. Instead, a slight increase in conductivity was shown.

Example 2: 2'FL Purification Using 2 MB Columns Compared to SAC+WBA Columns

A fermentation-based solution containing various salts, acids, color, human milk oligosaccharides, lactose and monomeric sugars was treated with two different ion exchange process systems including SAC, WBA and SBA resins. The first ion exchange system included one column, containing SAC resin, and one column, containing WBA resin, connected in series. The second ion exchange system included two identical mixed bed columns, containing SAC and SBA resins, connected in series. The SAC resin was Dowex88, the WBA resin was Dowex66, and the SBA resin was Dowex22.

Before the ion exchange process, the Dowex88 resin was regenerated with 5% sulfuric acid solution to the $H^+$ form, the Dowex66 resin was regenerated with 4% NaOH solution to the free base form and the Dowex22 resin was regenerated with 4% NaOH solution to the OH" form. After each resin regeneration step, all resins were flushed with water to remove excess regeneration chemicals before the ion exchange process. In the first ion exchange system, 100 mL of Dowex88 was packed into one column and 100 mL of Dowex66 was packed into second column. In the second ion exchange system, 50 mL of Dowex88 and 50 mL of Dowex22 were packed into two identical MB columns in alternating layers of the same volume. The flow rate in both ion exchange systems was 200 mL/h (2 BV/h), and the temperature was about 10° C.

The properties of the ion exchange feed solution are shown in Table 2-1. The same feed solution was used in both ion exchange systems. The properties of the outlet solution from SAC+WBA ion exchange system are shown in Table 2-2, and the properties of the outlet solution from the mixed bed ion exchange system are shown in Table 2-3.

TABLE 2-1

| Properties of the SAC + WBA ion exchange and MB ion exchange system feed | |
|---|---|
| Dry substance, g/100 g | 16.2 |
| pH | 7.05 |
| Conductivity, μS/cm | 5,170 |
| Color, ICUMSA | 78,163 |

TABLE 2-2

Properties of SAC + WBA ion exchange system outlet

| Outlet fraction, BV | Dry substance, g/100 g | pH | Conductivity, μS/cm | Color, ICUMSA |
|---|---|---|---|---|
| 0.0-0.5 | 3.20 | 9.02 | 17.0 | 1375 |
| 0.5-1.0 | 8.80 | 8.96 | 22.6 | N/A |
| 1.0-1.5 | 12.40 | 8.86 | 24.5 | N/A |
| 1.5-2.0 | 13.40 | 8.71 | 24.4 | N/A |
| 2.0-2.5 | 14.00 | 8.79 | 24.6 | 443 |
| 2.5-3.0 | 14.00 | 8.67 | 24.8 | N/A |
| 3.0-3.5 | 13.80 | 8.78 | 24.9 | N/A |
| 3.5-4.0 | 14.10 | 8.75 | 25.3 | N/A |
| 4.0-4.5 | 14.20 | 8.76 | 25.1 | 500 |
| 4.50-5.0 | 14.20 | 8.81 | 26.0 | N/A |
| 5.0-5.5 | 13.90 | 8.79 | 32.6 | N/A |
| 5.5-6.0 | 13.80 | 9.35 | 81.0 | 384 |
| 6.0-6.5 | 14.30 | 9.76 | 379.0 | 1119 |
| 6.5-7.0 | 15.70 | 9.67 | 1326.0 | 3842 |
| 7.0-7.5 | 16.00 | 9.23 | 2642.0 | 7000 |
| 7.5-8.0 | 16.30 | 8.80 | 3410.0 | 9061 |
| 8.0-8.5 | 16.30 | 8.40 | 3750.0 | 10890 |

TABLE 2-3

| Properties of mixed bed ion exchange system outlet | | | | |
|---|---|---|---|---|
| Outlet fraction, BV | Dry substance, g/100 g | pH | Conductivity, μS/cm | Color, ICUMSA |
| 0.0-0.5 | 0.00 | 6.97 | 2.4 | 0 |
| 0.5-1.0 | 1.30 | 6.55 | 1.3 | N/A |
| 1.0-1.5 | 5.30 | 6.30 | 1.6 | N/A |
| 1.5-2.0 | 7.40 | 5.99 | 1.2 | N/A |
| 2.0-2.5 | 10.20 | 6.13 | 1.1 | 2 |
| 2.5-3.0 | 11.60 | 6.03 | 1.2 | N/A |
| 3.0-3.5 | 12.40 | 5.97 | 1.6 | N/A |
| 3.5-4.0 | 13.60 | 6.03 | 0.7 | N/A |
| 4.0-4.5 | 14.30 | 6.13 | 0.8 | 3 |
| 4.50-5.0 | 14.60 | 6.00 | 0.8 | N/A |
| 5.0-5.5 | 14.40 | 5.94 | 0.9 | N/A |
| 5.5-6.0 | 14.90 | 5.99 | 0.9 | 9 |
| 6.0-6.5 | 14.90 | 5.69 | 0.9 | 30 |
| 6.5-7.0 | 14.80 | 5.57 | 1.1 | 120 |
| 7.0-7.5 | 15.00 | 5.03 | 1.9 | 333 |
| 7.5-8.0 | 14.90 | 4.72 | 4.0 | 773 |
| 8.0-8.5 | 15.00 | 4.23 | 10.4 | 1433 |

The mixed bed ion exchange column with the SAC and SBA resins was shown to remove conductivity further compared to SAC+WBA column system. In addition, with mixed bed system the pH of the column outlet product remained around 6, while with the SAC+WBA column system, the pH was close to 9 throughout the process.

Example 3: 2'FL Purification with a Single MB Column with Different SAC+SBA Resin Ratios A fermentation-based solution containing various salts, acids, color, human milk oligosaccharides, lactose and monomeric sugars, which was first treated with SAC and WBA resins in separate columns connected in series, was treated with two different ion exchange process systems including SAC and SBA resins. The ion exchange systems included a single mixed bed column, but with different ratios of SAC and SBA resins. The SAC resin was Dowex88, and the SBA resin was Dowex22.

Before the ion exchange process, the Dowex88 resin was regenerated with 5% sulfuric acid solution to the $H^+$ form, and the Dowex22 resin was regenerated with 4% NaOH solution to the $OH^-$ form. After each resin regeneration step, both resins were flushed with water to remove excess regeneration chemicals before the ion exchange process. In the first ion exchange system, 25 mL of Dowex88 resin and 25 mL of Dowex22 resin were packed into the MB column in alternating layers of the same volume. In the second ion exchange system, 15 mL of Dowex88 and 35 mL of Dowex22 were packed into the MB column in alternating layers of different volume. The flow rate in both ion exchange systems was 300 mL/h (6 BV/h). A temperature of less than 25° C. was used in both ion exchange systems.

The properties of the ion exchange feed solution are shown in Table 3-1. The same feed solution was used in both ion exchange systems. The properties of the outlet solution from the 25 mL SAC+25 mL SBA mixed bed ion exchange system are shown in Table 3-2, and the properties of the outlet solution from 15 mL SAC+35 mL SBA mixed bed ion exchange system are shown in Table 3-3.

TABLE 3-1

| Properties of the ion exchange feed solution | |
|---|---|
| Dry substance, g/100 g | 14.3 |
| pH | 3.20 |
| Conductivity, μS/cm | 385.0 |
| Color, ICUMSA | 934 |

TABLE 3-2

| Properties of SAC + SBA 50/50 volume ratio mixed bed ion exchange outlet | | | | |
|---|---|---|---|---|
| Outlet fraction, BV | Dry substance, g/100 g | pH | Conductivity, μS/cm | Color, ICUMSA |
| 0-2 | 10.33 | 6.60 | 0.69 | 4 |
| 2-4 | 13.68 | 5.63 | 0.89 | N/A |
| 4-6 | 13.92 | 3.96 | 14.95 | 37 |
| 6-8 | 13.98 | 3.36 | 107.5 | N/A |
| 8-10 | 14.04 | 3.04 | 217.9 | 228 |
| 10-12 | 14.04 | 2.93 | 292.2 | N/A |
| 12-14 | 14.10 | 2.87 | 349.0 | 298 |
| 14-16 | 14.04 | 2.81 | 381.0 | N/A |
| 16-18 | 14.16 | 2.81 | 397.0 | 325 |

TABLE 3-3

| Properties of SAC + SBA 30/70 volume ratio mixed bed ion exchange outlet | | | | |
|---|---|---|---|---|
| Outlet fraction, BV | Dry substance, g/100 g | pH | Conductivity, μS/cm | Color, ICUMSA |
| 0-2 | 10.64 | 5.93 | 0.58 | 8 |
| 2-4 | 13.56 | 6.13 | 0.60 | N/A |
| 4-6 | 13.86 | 6.28 | 0.80 | 7 |
| 6-8 | 13.92 | 6.05 | 1.26 | N/A |
| 8-10 | 13.98 | 4.28 | 12.21 | 52 |
| 10-12 | 13.98 | 3.53 | 64.6 | N/A |
| 12-14 | 14.04 | 3.23 | 141.4 | 271 |
| 14-16 | 14.10 | 3.09 | 206.8 | N/A |
| 16-18 | 14.10 | 2.97 | 255.3 | 333 |
| 18-20 | 14.10 | 2.95 | 291.1 | N/A |
| 20-22 | 14.16 | 2.94 | 316.9 | 367 |
| 22-24 | 14.16 | 2.90 | 341.0 | 374 |

The mixed bed ion exchange column with the SAC and SBA resins in a volume ratio of 30/70 showed greater capacity for the ion exchange of the feed solution compared to the mixed bed ion exchange column with the SAC and SBA resins in a volume ratio of 50/50. Approximately 4 BV cycle length was reached with the SAC+SBA 50/50 volume ratio mixed bed ion exchange system, while approximately 8 BV cycle length was reached with the SAC+SBA 30/70 volume ratio mixed bed ion exchange system. After these points, a clear conductivity and color breakthrough from the column was observed.

Example 4: 2'FL Purification with a Single MB Column with SAC+SBA and SAC+WBA Resins A fermentation-based solution containing various salts, acids, color, human milk oligosaccharides, lactose and monomeric sugars, which was first treated with SAC and WBA resins in separate columns connected in series, was treated with two different ion exchange process systems including SAC, WBA and SBA resins. Both ion exchange systems included a single mixed bed column with different resins. The SAC resin was Dowex88, the WBA resin was Dowex66, and the SBA resin was Dowex22.

Before the ion exchange process, the Dowex88 resin was regenerated with 5% sulfuric acid solution to the $H^+$ form, the Dowex66 resin was regenerated with 4% NaOH solution to the free base form, and the Dowex22 resin was regenerated with 4% NaOH solution to the $OH^-$ form. After each resin regeneration step, all resins were flushed with water to remove excess regeneration chemicals before the ion exchange process. In the first ion exchange system, 25 mL of the Dowex88 resin and 25 mL of the Dowex22 resin were packed into the MB column in alternating layers. In the second ion exchange system, 25 mL of the Dowex88 and 25 mL of the Dowex66 were packed into the MB column in alternating layers. The flow rate in both ion exchange systems was 150 mL/h (3 BV/h). A temperature of less than 25° C. was used in both ion exchange systems.

The properties of the ion exchange feed solution are shown in Table 4-1. The same feed solution was used in both ion exchange systems. The properties of the outlet solution from the 25 mL SAC+25 mL SBA mixed bed ion exchange system are shown in Table 4-2, and the properties of the outlet solution from the 25 mL SAC+25 mL WBA mixed bed ion exchange system are shown in Table 4-3.

TABLE 4-1

| Properties of the ion exchange feed solution | |
|---|---|
| Dry substance, g/100 g | 14.3 |
| pH | 3.20 |
| Conductivity, μS/cm | 385.0 |
| Color, ICUMSA | 934 |

TABLE 4-2

Properties of SAC + SBA mixed bed ion exchange system outlet

| Outlet fraction, BV | Dry substance, g/100 g | pH | Conductivity, μS/cm | Color, ICUMSA |
|---|---|---|---|---|
| 0-2 | 9.27 | 5.48 | 1.25 | 4 |
| 2-4 | 13.44 | 6.24 | 0.91 | N/A |
| 4-6 | 13.74 | 6.02 | 0.92 | 4 |
| 6-8 | 13.92 | 5.42 | 1.56 | N/A |
| 8-10 | 13.98 | 4.20 | 10.72 | 36 |
| 10-12 | 14.04 | 3.62 | 63.7 | N/A |
| 12-14 | 14.10 | 3.24 | 152.0 | 220 |
| 14-16 | 14.04 | 3.09 | 224.6 | N/A |
| 16-18 | 14.10 | 3.02 | 271.1 | 270 |
| 18-20 | 14.16 | 2.96 | 306.3 | N/A |
| 20-22 | 14.22 | 2.94 | 339.0 | 288 |

TABLE 4-3

Properties of SAC + WBA mixed bed ion exchange system outlet

| Outlet fraction, BV | Dry substance, g/100 g | pH | Conductivity, μS/cm | Color, ICUMSA |
|---|---|---|---|---|
| 0-2 | 10.27 | 5.16 | 0.95 | 8 |
| 2-4 | 13.32 | 5.83 | 0.93 | N/A |
| 4-6 | 13.86 | 4.07 | 11.15 | 33 |
| 6-8 | 13.92 | 3.34 | 97.5 | N/A |
| 8-10 | 14.04 | 3.10 | 205.4 | 221 |
| 10-12 | 14.10 | 3.02 | 258.3 | N/A |
| 12-14 | 14.10 | 2.95 | 295.4 | 248 |
| 14-16 | 14.10 | 2.91 | 329.0 | N/A |
| 16-18 | 14.16 | 2.90 | 350.0 | 275 |
| 18-20 | 11.87 | 2.89 | 289.0 | 320 |

Both ion exchange systems were shown to adjust pH closer to neutral and lower the conductivity within their capacity range. Approximately 8 BV cycle length was reached with the SAC+SBA mixed bed ion exchange system, while approximately 4 BV cycle length was reached with the SAC+WBA mixed bed ion exchange system. After these points, a clear conductivity and color breakthrough from the column was observed.

Example 5: 2'FL Purification with 3 MB Columns

A fermentation-based solution containing various salts, acids, color, human milk oligosaccharides, lactose and monomeric sugars was treated with an ion exchange process system including SAC and SBA resins. The system included three mixed bed columns connected in series. The SAC resin was Dowex88, and the SBA resin was Dowex22.

Before the ion exchange process, the Dowex88 resin for the MB column was regenerated with 5% sulfuric acid solution to the $H^+$ form, and the Dowex22 resin for the MB columns was regenerated with 4% NaOH solution to the $OH^-$ form. After each resin regeneration step, all resins were flushed with water to remove excess regeneration chemicals. The Dowex88 and Dowex22 resins were packed into the MB column in alternating layers of the same volume.

The ion exchange system included two mixed bed columns containing 40 mL of SAC resin and 60 mL of SBA resin and one mixed bed column containing 33 mL of SAC resin and 33 mL of SBA resin. The flow rate in ion exchange system was 250 mL/h (2.5 BV/h). The temperature in the ion exchange system was 10° C.

The properties of the ion exchange feed solution are shown in Table 5-1. The properties of the outlet solution from MB+MB+MB ion exchange system are shown in Table 5-2.

TABLE 5-1

| Properties of the ion exchange feed solution | |
|---|---|
| Dry substance, g/100 g | 14.4 |
| pH | 6.46 |
| Conductivity, μS/cm | 6,885 |
| Color, ICUMSA | 16,633 |

TABLE 5-2

Properties of MB + MB + MB ion exchange system outlet

| Outlet fraction, BV | Dry substance, g/100 g | pH | Conductivity, μS/cm | Color, ICUMSA |
|---|---|---|---|---|
| 0-2 | 7.57 | 5.39 | 0.82 | N/A |
| 2-4 | 11.32 | 5.67 | 0.93 | 4 |
| 4-6 | 11.62 | 5.56 | 0.59 | 5 |
| 6-7 | 11.81 | 5.61 | 0.54 | N/A |
| 7-8 | 11.99 | 5.65 | 0.56 | 5 |
| 8-9 | 11.99 | 5.75 | 0.60 | N/A |
| 9-10 | 11.99 | 5.57 | 1.06 | N/A |
| 10-11 | 12.05 | 3.70 | 52.80 | 120 |
| 11-12 | 12.29 | 2.80 | 503.00 | 996 |
| 12-13 | 12.72 | 2.47 | 1157.00 | N/A |

Approximately 10 BV cycle length was reached with the MB+MB+MB ion exchange system. At this point, a clear conductivity breakthrough from the last column was observed. The pH of the combined product within 0-10 BV in the MB+MB+MB system was 5.60.

We claim:

1. A process for preparing a purified human milk oligosaccharide (HMO) from an HMO solution comprising the HMO being purified and at least one non-HMO fermentation-derived component, wherein:

the process comprises passing the HMO solution through a mixed bed ion exchange vessel comprising a combination of cation ion exchange material with anion ion exchange material, the process is carried out in the absence of any ion exchange vessel that comprises cation ion exchange material without also comprising anion ion exchange material, and the process is carried out in the absence of any ion exchange vessel that comprises anion ion exchange material without also comprising cation ion exchange material;

wherein the HMO solution is obtained from a fermentation process; and wherein the purified human milk oligosaccharide is obtained.

2. A process according to claim 1, wherein the mixed bed ion exchange vessel comprises a column packed with a uniform mixture of the cation ion exchange material and the anion ion exchange material.

3. The process according to claim 1, wherein the mixed bed ion exchange vessel comprises a column packed with alternating layers of the anion ion exchange material and the cation ion exchange material.

4. The process according to claim 3, wherein the alternating layers each have the same volume.

5. The process of claim 1, wherein:

each cation ion exchange material comprises cation ion exchange resin, and each anion ion exchange material comprises anion ion exchange resin.

6. The process of claim 1, wherein:

the cation ion exchange material in the mixed bed ion exchange vessel comprises a strong acid cation (SAC) exchange material, and the anion ion exchange material in the mixed bed ion exchange vessel comprises a strong base anion (SBA) exchange material.

7. The process of claim 1, wherein:

the cation ion exchange material in the mixed bed ion exchange vessel comprises a strong acid cation (SAC) exchange material, and the anion ion exchange material in the mixed bed ion exchange vessel comprises a weak base anion (WBA) exchange material.

8. The process of claim 1, wherein:

the cation ion exchange material in the mixed bed ion exchange vessel comprises a weak acid cation (WAC) exchange material, and the anion ion exchange material in the mixed bed ion exchange vessel comprises a weak base anion (WBA) exchange material.

9. The process of claim 1, wherein:

the cation ion exchange material in the mixed bed ion exchange vessel comprises a weak acid cation (WAC) exchange material, and the anion ion exchange material in the mixed bed ion exchange vessel comprises a strong base anion (SBA) exchange material.

10. The process of claim 1, wherein the cation ion exchange material and the anion ion exchange material are present in the mixed bed ion exchange vessel at a volume ratio of from about 50:50 to about 30:70.

11. The process of claim 1, wherein no base is added to the HMO solution downstream of the mixed bed ion exchange before the HMO solution is passed through an enzymatic treatment, ultrafiltration, nanofiltration, sterile filtration, electrodialysis, chromatography, an antifoam removal step, activated carbon, crystallization or spray-drying.

12. The process of claim 1, wherein no base is added to the human milk solution or purified HMO downstream of the mixed bed ion exchange.

13. The process of claim 1, wherein no acid is added to the HMO solution downstream of the mixed bed ion exchange before the HMO solution is passed through an enzymatic treatment, ultrafiltration, nanofiltration, sterile filtration, electrodialysis, chromatography, an antifoam removal step, activated carbon, crystallization or spray-drying.

14. The process of claim 1, wherein no acid is added to the human milk solution or purified HMO downstream of the mixed bed ion exchange.

15. The process of claim 1, wherein the process comprises a single mixed bed ion exchange vessel.

16. The process of claim 1, wherein the process comprises two mixed bed ion exchange vessels.

17. The process according to claim 16, wherein the two mixed bed ion exchange vessels are in series.

18. The process of claim 1, wherein the process comprises three mixed bed ion exchange vessels.

19. The process of claim 1, wherein the HMO solution further comprises:

an ingredient selected from monovalent and divalent salts, lactose, oligosaccharides besides the HMO being purified, monosaccharides, amino acids, polypeptides, proteins, organic acids and nucleic acids.

20. The process of claim 1, wherein the HMO solution further comprises:

an ingredient selected from a salt, an acid, human milk oligosaccharides besides the HMO being purified, lactose and monomeric sugars.

21. The process of claim 1, wherein the HMO is 2'-fucosyllactose.

22. The process of claim 1, wherein the HMO is 3-fucosyllactose.

23. A purified HMO obtained by the process of claim 1.

24. The process of claim 1, wherein the cation-exchange and anion-exchange materials are simultaneously contacted with the HMO solution in the same column, and not passed sequentially through separate columns.

25. The process of claim 1, wherein the process is carried out without the use of any cation-exchange column or anion-exchange column, and the HMO solution is passed exclusively through a single mixed-bed column.

26. The process of claim 1, wherein the purified HMO has a higher purity and yield than HMO purified using a method involving separate cation and anion exchange columns.

* * * * *